(12) United States Patent
Matov et al.

(10) Patent No.: US 7,844,429 B2
(45) Date of Patent: Nov. 30, 2010

(54) SYSTEM AND METHOD FOR THREE-DIMENSIONAL COMPLETE TOOTH MODELING

(75) Inventors: Vadim Matov, San Jose, CA (US); Jihua Cheng, Cupertino, CA (US)

(73) Assignee: Align Technology, Inc., San Jose, CA (US)

( * ) Notice: Subject to any disclaimer, the term of this patent is extended or adjusted under 35 U.S.C. 154(b) by 1168 days.

(21) Appl. No.: 11/458,485

(22) Filed: Jul. 19, 2006

(65) Prior Publication Data
US 2008/0020350 A1    Jan. 24, 2008

(51) Int. Cl.
*G06F 19/00* (2006.01)
*G06G 7/48* (2006.01)
*A61C 11/00* (2006.01)
*A61C 3/00* (2006.01)
*G06T 17/00* (2006.01)

(52) U.S. Cl. .................. 703/7; 433/213; 433/24; 345/420; 700/118; 700/98

(58) Field of Classification Search .................. 433/213, 433/24; 703/7; 700/98; 345/418–420
See application file for complete search history.

(56) References Cited

U.S. PATENT DOCUMENTS

| | | | | |
|---|---|---|---|---|
| 2,307,646 | A | * | 1/1943 | Sonne .............................. 396/8 |
| 5,121,333 | A | * | 6/1992 | Riley et al. .................. 700/163 |
| 5,549,476 | A | * | 8/1996 | Stern ........................... 433/223 |
| 5,691,905 | A | * | 11/1997 | Dehoff et al. ................. 700/98 |
| 5,886,702 | A | * | 3/1999 | Migdal et al. ............... 345/423 |
| 5,975,893 | A | | 11/1999 | Chishti et al. |
| 6,049,743 | A | * | 4/2000 | Baba ........................... 700/163 |
| 6,227,850 | B1 | * | 5/2001 | Chishti et al. .................. 433/24 |

(Continued)

FOREIGN PATENT DOCUMENTS

JP          09019443          7/1995

OTHER PUBLICATIONS 3D whole tooth model from CT Volume using thin-plate splines, by Sheng-hui Liao; Ruo-feng Tong; Jin-xiang Dong; Computer Supported Cooperative Work in Design, 2005. Proceedings of the Ninth International Conference on vol. 1, May 24-26, 2005 pp. 600-604 vol. 1.*

*Primary Examiner*—Hugh Jones
*Assistant Examiner*—Akash Saxena
(74) *Attorney, Agent, or Firm*—Brooks, Cameron & Huebsch, PLLC

(57) ABSTRACT

A system and method for modeling of complete tooth, including root and crown, of a patient to facilitate orthodontic treatment are provided, wherein a generic tooth modeling is combined with a tooth crown modeling for a patient to yield a complete tooth modeling. A generic tooth three-dimensional model for a particular tooth is morphed with a three-dimensional model of a patient's crown for the corresponding tooth to yield a complete three-dimensional model for that tooth. Modeling techniques can be conducted with computer-based systems, such as systems configured for storing patient data and generic tooth data, morphing such data and/or facilitating additional orthodontic treatment applications, through the use of one or more algorithms. Adjustment of the complete tooth model for the tooth can be provided through additional patient information, such as X-ray imaging, to address variations in root shape between a generic root and an actual root shape for a patient.

37 Claims, 14 Drawing Sheets

U.S. PATENT DOCUMENTS

| | | | |
|---|---|---|---|
| 6,386,878 B1 | 5/2002 | Pavlovskaia et al. | |
| 6,409,504 B1 | 6/2002 | Jones et al. | |
| 6,463,344 B1 * | 10/2002 | Pavloskaia et al. | 700/98 |
| 6,514,074 B1 | 2/2003 | Chishti et al. | |
| 6,685,469 B2 | 2/2004 | Chishti et al. | |
| 6,733,289 B2 * | 5/2004 | Manemann et al. | 433/24 |
| 7,040,896 B2 | 5/2006 | Pavlovskaia et al. | |
| 7,329,122 B1 * | 2/2008 | Scott | 433/24 |
| 7,476,100 B2 * | 1/2009 | Kuo | 433/6 |
| 7,728,848 B2 * | 6/2010 | Petrov et al. | 345/619 |
| 2001/0002310 A1 * | 5/2001 | Chishti et al. | 433/24 |
| 2001/0056308 A1 * | 12/2001 | Petrov et al. | 700/98 |
| 2002/0037489 A1 * | 3/2002 | Jones et al. | 433/24 |
| 2002/0055800 A1 * | 5/2002 | Nikolskiy et al. | 700/98 |
| 2002/0064759 A1 * | 5/2002 | Durbin et al. | 433/213 |
| 2003/0027098 A1 * | 2/2003 | Manemann et al. | 433/24 |
| 2003/0068598 A1 * | 4/2003 | Vallittu et al. | 433/167 |
| 2004/0023188 A1 * | 2/2004 | Pavlovskaia et al. | 433/215 |
| 2005/0042569 A1 * | 2/2005 | Phan et al. | 433/24 |
| 2005/0043837 A1 * | 2/2005 | Rubbert et al. | 700/98 |
| 2006/0063135 A1 * | 3/2006 | Mehl | 433/223 |
| 2006/0111631 A1 * | 5/2006 | Kelliher et al. | 600/425 |
| 2006/0147872 A1 * | 7/2006 | Andreiko | 433/24 |
| 2006/0275736 A1 * | 12/2006 | Wen et al. | 433/213 |
| 2007/0054231 A1 * | 3/2007 | Manemann et al. | 433/24 |
| 2008/0020350 A1 * | 1/2008 | Matov et al. | 433/213 |
| 2008/0154419 A1 * | 6/2008 | Cheng et al. | 700/118 |
| 2009/0148809 A1 * | 6/2009 | Kuo et al. | 433/68 |
| 2009/0246726 A1 * | 10/2009 | Chelnokov et al. | 433/24 |
| 2010/0167243 A1 * | 7/2010 | Spiridonov et al. | 433/224 |

* cited by examiner

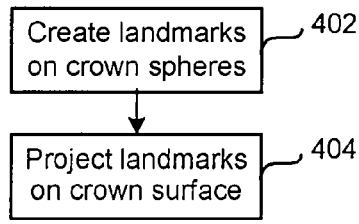
FIG. 4A
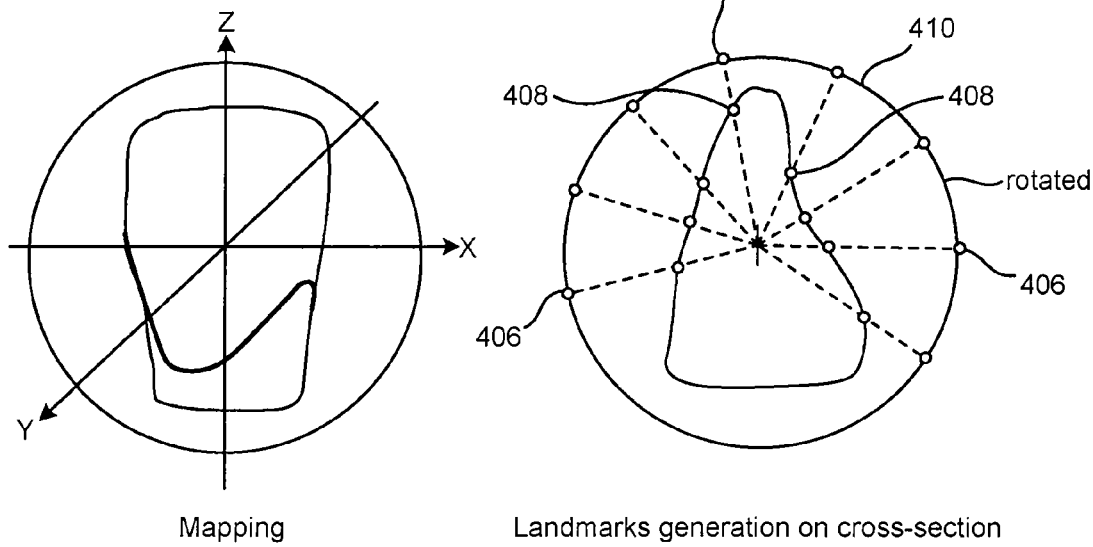
Mapping  
FIG. 4B
Landmarks generation on cross-section  
FIG. 4C
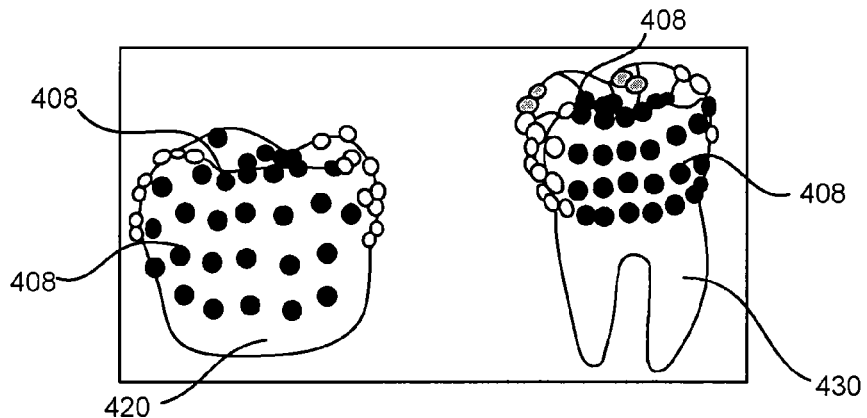
FIG. 4D

FIG. 6D Mapping — Step 1

FIG. 6C Root Mesh

FIG. 6E Merged Loop — Step 2

FIG. 6F Re-triangulation and Stitching — Step 3

602 Project 3D loops onto X-Y plane
604 Construct merged loop
606 Retriangulate crown mesh and root mesh
608 Merge crown mesh and root mesh

FIG. 6B Crown Mesh

Stitching with smoothing

Stitching without smoothing

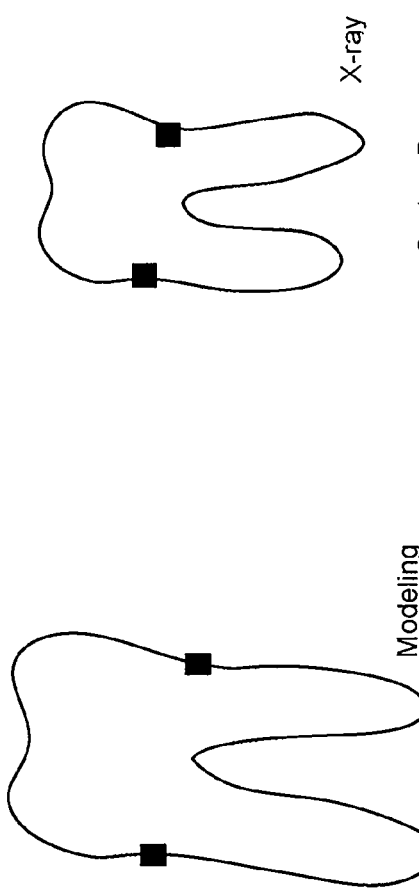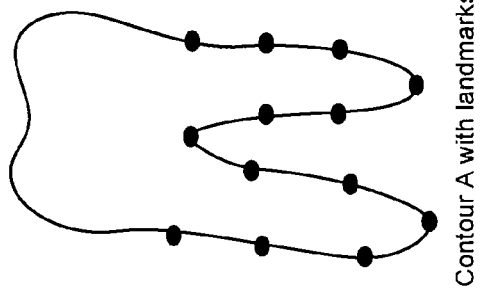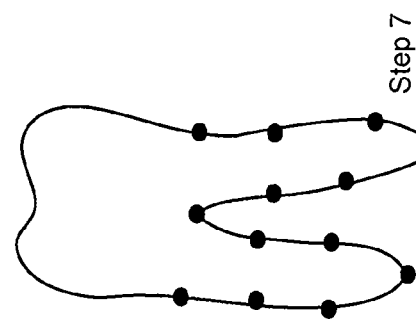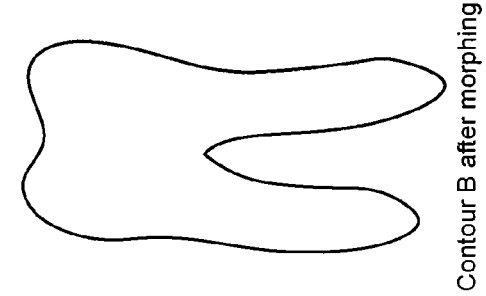
FIG. 11B Contour A — Modeling
FIG. 11C Contour B — X-ray
FIG. 11D Contour A with landmarks
FIG. 11E Contour B after scaling with landmarks — Step 7
FIG. 11F Contour B after morphing

US 7,844,429 B2

SYSTEM AND METHOD FOR THREE-DIMENSIONAL COMPLETE TOOTH MODELING

TECHNICAL FIELD

The present invention relates, generally, to dental and/or orthodontic treatment, and in particular to a system and method for three-dimensional modeling of a complete tooth and/or teeth, including root and crown, of a patient to facilitate dental and/or orthodontic treatment.

BACKGROUND OF THE INVENTION

The ability to provide an accurate and complete modeling of teeth is an important element in the growing field of computational orthodontics and other computer aided dental treatment systems. Current techniques for impression-based computational orthodontics are limited to crown modeling of the patient's tooth, such as the capturing of crown and gum shape information, but do not capture or utilize corresponding root information. As a result, such impression techniques do not provide for the root component within the present tooth model, and fail to account for root movement and/or interaction within the gums, thus limiting the ability of the complete tooth model in facilitating orthodontic treatment. Such failure to account for root movement can also result in root collision that hinders the orthodontic treatment process.

A complete tooth model, comprising both root and crown components for each tooth, could be extremely beneficial for providing optimum diagnostics, treatment planning and analysis, such as for example, in stage planning and simulation, collision detection, finite element analysis, biometrics and mass property calculations to name a few.

SUMMARY OF THE INVENTION

In accordance with various aspects of the present invention, a system and method for three-dimensional modeling of a complete tooth and/or teeth, including both root and crown, of a patient to facilitate dental and/or orthodontic treatment are provided, wherein a generic tooth model comprising generic root and crown components is combined with a crown-only model of one or more actual teeth of a patient to yield a complete tooth model comprising both root and crown components. In accordance with an exemplary embodiment, a generic tooth three-dimensional model for a particular tooth is generated and then automatically morphed with a three-dimensional model of a patient's actual crown for the corresponding tooth to yield a complete three-dimensional model for that tooth. Such a process can be suitably applied for any and all of the various teeth within a patient, such as molars, bicuspids, canines or any other teeth within a patient. Various exemplary embodiments can comprise methods and systems for automated generation of morphing landmarks, model segmentation, root and crown stitching and/or three-dimensional root model adjustment. Such modeling techniques can be conducted with one or more computer-based systems, such as systems configured for storing actual patient data and generic tooth data, morphing generic tooth data to such patient's data and/or facilitating additional orthodontic treatment applications, through the use of one or more algorithms.

In accordance with an exemplary embodiment, further adjustment of the complete tooth model for the tooth can be provided through additional patient information regarding the actual root and/or crown, such as X-ray imaging and the like, to address variations in root shape between a morphed generic root and an actual root shape for a patient so as to yield a root shape on the tooth model which more closely approximates the actual root shape of the actual tooth.

BRIEF DESCRIPTION OF THE DRAWINGS

The exemplary embodiments of the present invention will be described in connection with the appended drawing figures in which like numerals denote like elements, and wherein:

FIGS. 4A-4D illustrate a flow diagram and graphical representations of an exemplary method of automatic landmark generation for tooth crown in accordance with an exemplary embodiment of the present invention;

FIGS. 6A-6F illustrate a flow diagram and graphical representations and curves for an exemplary method for automatic stitching of the crown with the root in accordance with an exemplary embodiment of the present invention;

FIGS. 11A-11F illustrate an exemplary flow diagram and graphical representations for automatic complete tooth model adjustment using X-ray data in accordance with an exemplary embodiment of the present invention.

DETAILED DESCRIPTION

The present invention may be described herein in terms of various components and processing steps. It should be appreciated that such components and steps may be realized by any number of hardware and software components configured to perform the specified functions. For example, the present invention may employ various electronic control devices, visual display devices, input terminals and the like, which may carry out a variety of functions under the control of one or more control systems, microprocessors or other control devices. In addition, the present invention may be practiced in any number of orthodontic or dental contexts and the exemplary embodiments relating to a system and method for modeling of complete tooth of a patient as described herein are merely a few of the exemplary applications for the invention. For example, the principles, features and methods discussed may be applied to any orthodontic or dental treatment application or process.

It should be noted that for illustrative purposes, the various exemplary methods and systems may be described in connection with a single tooth of a patient; however, it should be understood that such exemplary methods and systems can be suitably implemented on more than one tooth and/or all teeth within a patient, such as molars, bicuspids, canines or any other teeth within a patient. For example, the exemplary methods and systems can be suitably implemented by performing a particular process, operation or step on one or more teeth before proceeding to a subsequent process, operation or step, or by performing all or essentially all processes, operations or steps on a particular tooth before proceeding to another tooth, or any combination thereof.

Figure 1A:
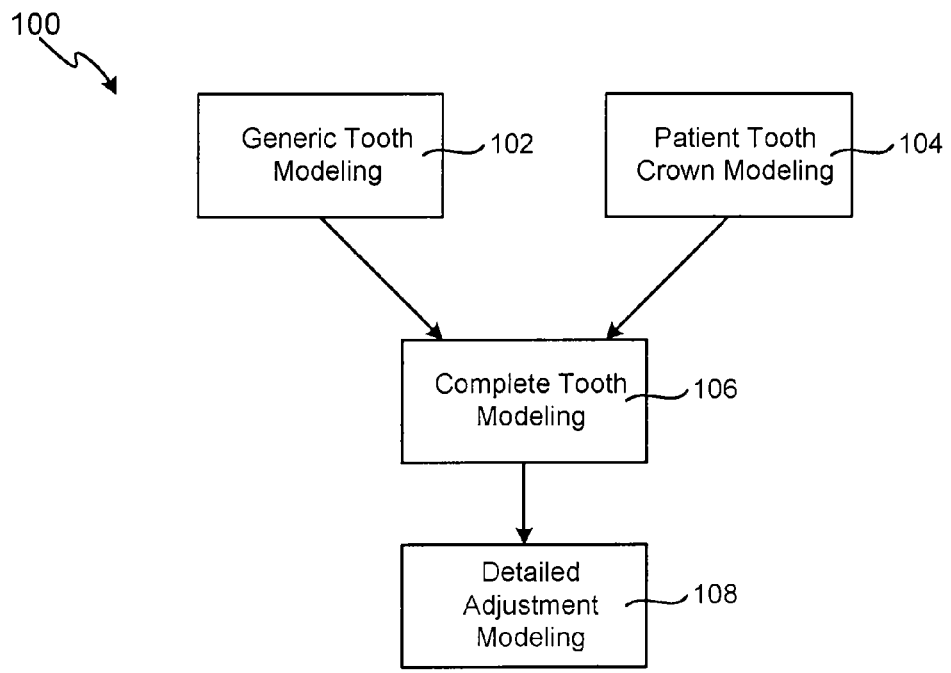
FIGS. 1A-1C illustrate diagrams of an exemplary system and method for modeling of tooth root and crown of a patient in accordance with an exemplary embodiment of the present invention.
Figure 1B:
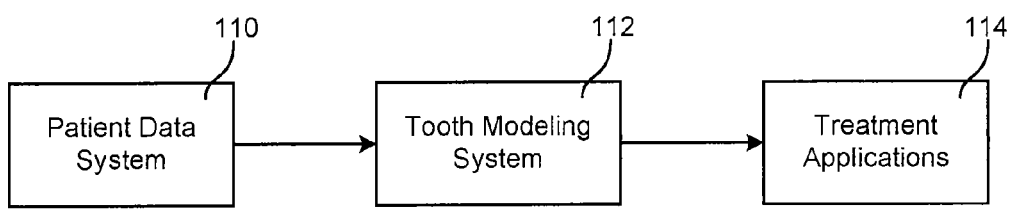
Figure 1C:
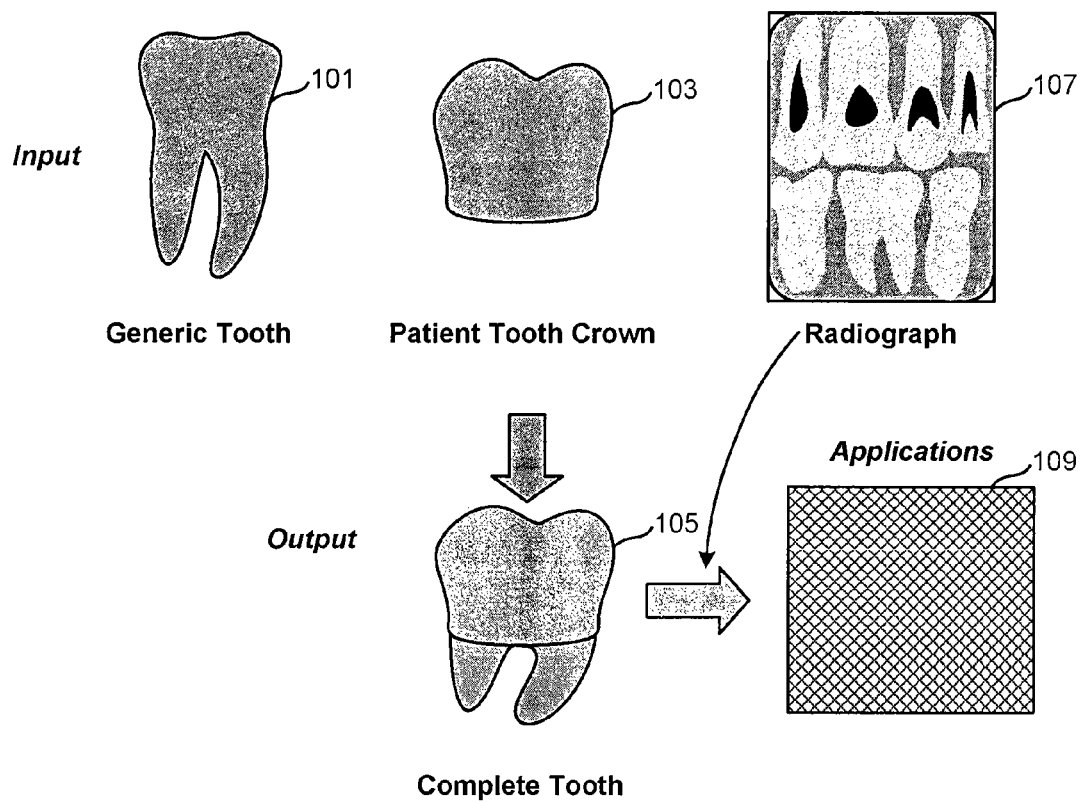

In accordance with various aspects of the present invention, a system and method for modeling of complete tooth, including root and crown, of a patient to facilitate orthodontic treatment are provided, wherein a generic tooth model is combined with a corresponding tooth crown model for a patient to yield a complete tooth modeling. For example, with reference to FIGS. 1A-1C, in accordance with an exemplary embodiment, a system for modeling tooth root and crown 100 comprises a generic tooth three-dimensional model 102 for an exemplary tooth configured for combination with a three-dimensional model 104 of a patient's crown for the corresponding tooth to yield a complete three-dimensional model 106 for that tooth. Generic tooth model 102 is configured to provide a generic three-dimensional modeling of both root and crown for a particular tooth of a patient, such as generic tooth model 101. In a preferred embodiment, generic tooth model 102 will be of the same type of tooth (e.g. molar, canine, bicuspid and the like) as the actual tooth it is intended to model. Moreover, in other exemplary embodiments, generic tooth model 102 can be the same numbered tooth as the actual patient tooth, using conventional tooth numbering and identification systems. Patient tooth crown model 104 can be suitably generated by various techniques for tooth crown modeling to generate a three-dimensional patient tooth crown 103, such as those disclosed in U.S. Pat. No. 6,685, 469, assigned to Align Technology, Inc. (the "'469 Patent"), or such modeling processes known and provided under the brands INVISALIGN® and CLINCHECK® that are available under Align Technology, Inc. of Santa Clara, Calif. The creation of complete tooth model 106 can be suitably realized by an automated morphing of generic tooth modeling 102 and patient tooth crown model 104, such as by a computer algorithm within a tooth model system 112, for the creation of a three-dimensional complete tooth 105, with such processes being applied to any or all teeth within the patient.

The exemplary modeling methods can be conducted with one or more computer-based systems, such as a system 110 configured for storing patient data and generic tooth data, a tooth modeling system 112 configured for generating generic tooth model 102 and patient tooth crown model 104 and for morphing data and information from model 102 and model 104 to generate complete tooth model 106, and a system 114 configured for facilitating any other conventional orthodontic treatment applications, such as methods or processes for tracking teeth movement and position, evaluating gingival effects, or any other orthodontic treatment process from pre-treatment to final stages, or any stages in between. Systems 110, 112 and/or 114 can comprise one or more microprocessors, memory systems and/or input/output devices for processing modeling data and information. To facilitate modeling of root and crown of a patient, tooth modeling system 112 can comprise one or more software algorithms configured for generating complete tooth model 106 and/or performing other functions set forth herein.

In accordance with an exemplary embodiment, further adjustment of the complete tooth model for the tooth can be provided through detailed adjustment modeling 108. For example, additional patient information regarding the actual root of a patient, such as X-ray imaging information provided from a radiograph 107, can be suitably utilized by tooth modeling system 112 to address variations in root shape between a generic root and an actual root shape for a patient so as to yield a root shape on complete tooth model 105 which more closely approximates the actual root shape of the actual tooth. Such additional actual root information can comprise various formats and generated in various manners. For example, X-ray imaging information can comprise, for example, panoramic, periapical, bitewing, cephalometric or other like information, for facilitating further detailed modeling.

Figure 2:
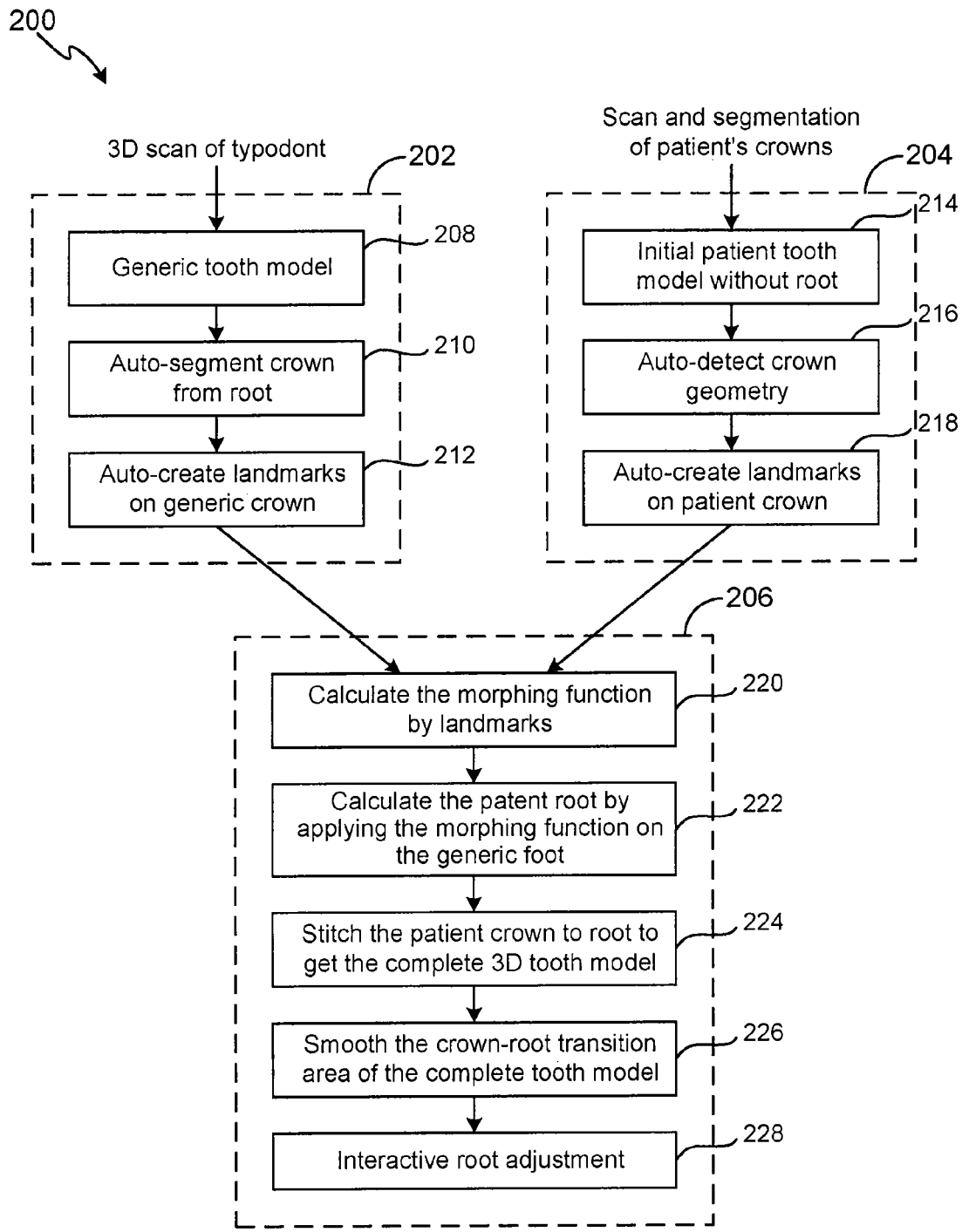
FIG. 2 illustrates a flow diagram of an exemplary method of tooth modeling in accordance with an exemplary embodiment of the present invention.

With reference to FIG. 2, a flow diagram illustrates an exemplary computer-implemented method 200 for modeling of tooth root and crown of a patient comprises a method 202 for generating a generic tooth model, a method 204 for generating a patient tooth crown model, and a method 206 for generating a complete tooth model through combination of a morphed generic root model with a corresponding patient tooth crown model. Method 200 can be suitably utilized to provide both generic tooth models and crown tooth models for each tooth of a patient, thus enabling a complete tooth model for any and/or all teeth of a patient to be obtained for facilitating orthodontic treatment.

Generic tooth modeling method 202 is configured to provide a reference for construction for complete tooth modeling, such as the generation of a generic tooth 101 comprising both root and crown for a particular tooth. In accordance with an exemplary embodiment, generic tooth modeling 202 comprises the generation of a generic tooth model template (208), auto-segmenting of a generic crown from the generic root within the generic tooth model (210), and automatic creation of landmarks on the generic crown (212).

Generating of a generic tooth model template (208) is configured to facilitate the creation of landmarks on the generic tooth model to allow for morphing with the patient tooth crown model. For example, in order to generate adequately distributed landmarks and to accurately segment the crown from the tooth, the setup of generic teeth data is provided to generate a generic tooth template. With reference to a flow diagram illustrated in FIG. 3A, in accordance with an exemplary embodiment, a process 300 for generating of a generic tooth model template can comprise the acquisition of data from a physical tooth model (302), the decimating of tooth model data (304), the setting up a generic tooth coordinate system (306), the constructing of a generic tooth digital model (308), the identifying of gingival curves (310) and the creating of template file(s) associated with the generic teeth (312). The acquisition of data from a physical tooth model data (302) can comprise the scanning of a standard typodont or any other three-dimensional models for demonstrating alignment of teeth within a patient to generate three-dimensional digital template data.

Such typodont or models that are used for scanning can comprise both an exemplary root and crown for a single tooth or multiple teeth of a patient. In addition, such typodont or generic models can be suitably provided based on different configurations of teeth, e.g., different sizes, shapes, and/or caps, different types of teeth such as molars, bicuspids or canines, and/or different occlusal patterns or characteristics, e.g., overbite, underbite, skewed or other like misalignment patterns. In accordance with an exemplary embodiment, the root shape, configuration or component for such typodont models can comprise the same generic root configuration for all types of teeth. In accordance with other exemplary embodiments, the root component for such typodont models can comprise a typical generic root configuration for a type of tooth, e.g., a typical root shape or configuration for molars, bicuspids and/or canines can be provided, based on one type for all patients, or based on whether the patient is a child or adult, male or female, or any other demographic or characteristic that might be associated with different types of teeth. Moreover, in accordance with other exemplary embodiments, the root component for such typodont models can comprise a typical generic root shape or configuration for a specific actual tooth, e.g., a specific root shape for a particular canine tooth can be used with the specific crown shape for that particular canine tooth to generate the typodont model, again based on one configuration for that particular tooth all patients, or based on different configurations for that specific tooth depending on whether the patient is a child or adult, male or female, or any other demographic or characteristic that might be associated with different types of teeth.

As such, generic models for any type of teeth characteristic or type can be provided and suitably utilized, allowing great flexibility in specializing for different teeth structures, occlusal patterns and characteristics of a patient. In addition, any conventional devices, systems and/or methods for the scanning of physical models, such as typodonts, to generate data can be utilized, such as known techniques for generating initial digital data sets (IDDS), including that set forth in U.S. Pat. No. 6,217,325, assigned to Align Technology, Inc.

To reduce the amount of data and/or filter out any undesirable data after such acquisition of data from the typodont or generic tooth model, the decimating of data (304) can be conducted, such as the removal or deletion of data or otherwise the finding of optimal data values through the elimination at a constant fraction of the scanning data; however, the decimating of data (304) can also be suitably omitted or otherwise replaced by any filtering or data enhancement techniques.

Figures 3A, 3B, 3C:
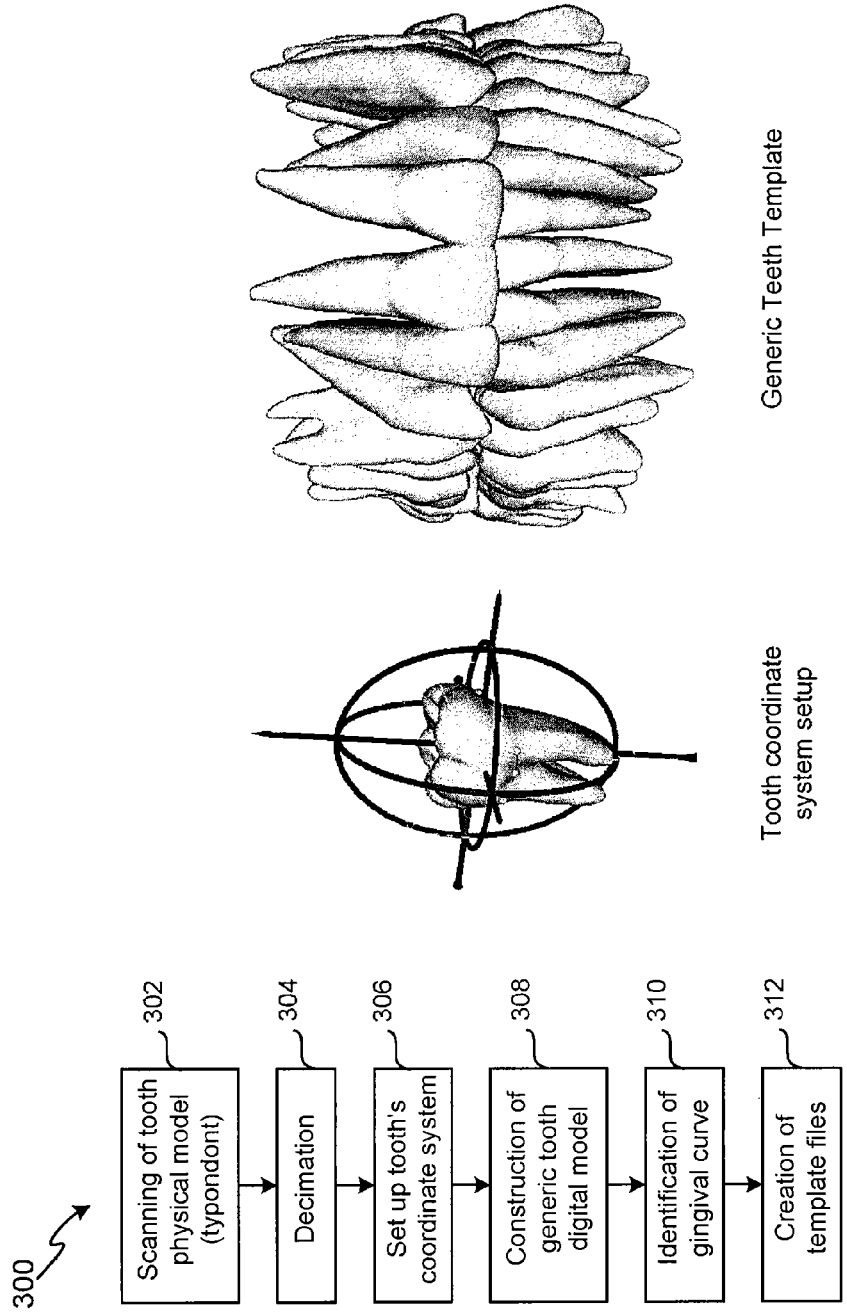
FIGS. 3A-3C illustrate a flow diagram and graphical representations of an exemplary method of modeling a generic teeth template in accordance with an exemplary embodiment of the present invention.

Whether or not the scanned data is decimated, the developing of a generic tooth coordinate system (306) can be undertaken, such as to setup or develop a generic tooth coordinate system as illustrated in FIG. 3B. The coordinate system can be set-up automatically and/or adjusted manually, using any conventional or later developed techniques for setting up coordinate systems of an object. Upon generation of a coordinate system for a generic tooth, the constructing of a digital generic tooth model (308) comprising root and crown can be conducted for an individual tooth and/or two or more teeth. Such constructing of digital tooth models can comprise any methodology or process for converting scanned data into a digital representation. Such methodology or processes can include, for example, those disclosed in U.S. Pat. No. 5,975,893, entitled "Method and System for Incrementally Moving Teeth" assigned to Align Technology, Inc. For example, with reference to an overall method for producing the incremental position adjustment appliances for subsequent use by a patient to reposition the patient's teeth as set forth in U.S. Pat. No. 5,975,893, as a first step, a digital data set representing an initial tooth arrangement is obtained, referred to as the IDDS. Such an IDDS may be obtained in a variety of ways. For example, the patient's teeth may be scanned or imaged using well known technology, such as X-rays, three-dimensional x-rays, computer-aided tomographic images or data sets, magnetic resonance images, etc. Methods for digitizing such conventional images to produce data sets are well known and described in the patent and medical literature. By way of example, one approach is to first obtain a plaster cast of the patient's teeth by well known techniques, such as those described in Graber, Orthodontics: Principle and Practice, Second Edition, Saunders, Philadelphia, 1969, pp. 401-415. After the tooth casting is obtained, it can be digitally scanned using a conventional laser scanner or other range acquisition system to produce the IDDS. The data set produced by the range acquisition system may, of course, be converted to other formats to be compatible with the software which is used for manipulating images within the data set. General techniques for producing plaster casts of teeth and generating digital models using laser scanning techniques are described, for example, in U.S. Pat. No. 5,605,459.

After constructing of the generic tooth digital model (308), the identifying of the gingival curve (310) can be conducted to identify the gum lines and/or root association. Such identification can comprise any conventional computational orthodontics methodology or process for identification of gingival curves, now known or hereinafter derived. For example, the methodologies and processes for identification of gingival curves can include those disclosed in U.S. Pat. No. 7,040,896, entitled "Systems and Methods for Removing Gingiva From Computer Tooth Models", and assigned to Align Technology, Inc. (the "'896 Patent") and U.S. Pat. No. 6,514,074, entitled "Digitally Modeling the Deformation of Gingival", and assigned to Align Technology, Inc. (the "'074 Patent"), and the various patents disclosed in the '896 and '074 Patents. In the '896 Patent, for example, such a process for identification of gingival curves can comprise a computer-implemented method separates a tooth from an adjacent structure, such as a gingiva, by defining a cutting surface, and applying the cutting surface between the tooth and the structure to separate the tooth in a single cut. In the '074 Patent, for example, such a process for identification of gingival curves can comprise having a computer obtain a digital model of a patient's dentition, including a dental model representing the patient's teeth at a set of initial positions and a gingival model representing gum tissue surrounding the teeth, wherein the computer then derives from the digital model an expected deformation of the gum tissue as the teeth move from the initial positions to another set of positions.

Having constructed the digital generic tooth model (308) and identified the gingival curve (310), one or more generic tooth template files can be created (312), such as the exemplary generic teeth template illustrated in FIG. 3C comprising substantially a complete set of teeth of a patient. Such generic teeth templates can then be suitably utilized to allow for segmenting of crowns and landmark distribution on the generic teeth. In addition, such generic teeth templates can be suitably utilized for one or more treatments, and/or replaced or updated with other generic teeth templates as desired. Moreover, such generic teeth templates can be suitably created and/or stored for later use, and can be configured for various differences in patients, such as for children-based templates and adult-based templates, with the ability to have a plurality of templates that are specially created for the different types of teeth and related characteristics, sizes, shapes, and occlusal patterns or other features.

With reference again to FIG. 2, after generic teeth templates have been generated, automated segmenting of a generic crown from the generic root within the generic tooth template (210) can be conducted to prepare the generic tooth template for landmark creation. In this process, the crown portion of the generic tooth template is suitably parceled out and/or identified to allow mapping during landmark processes.

Figure 5B:
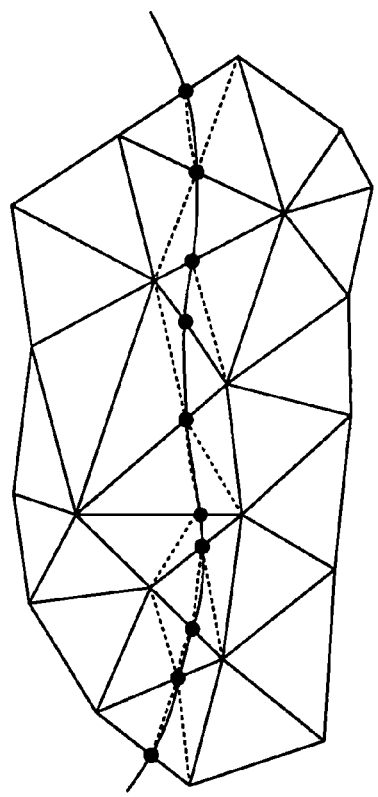
FIGS. 5A and 5B illustrate a flow diagram and a graphical representation for an exemplary method for root and crown mesh generation in accordance with an exemplary embodiment of the present invention.
Figure 5A:
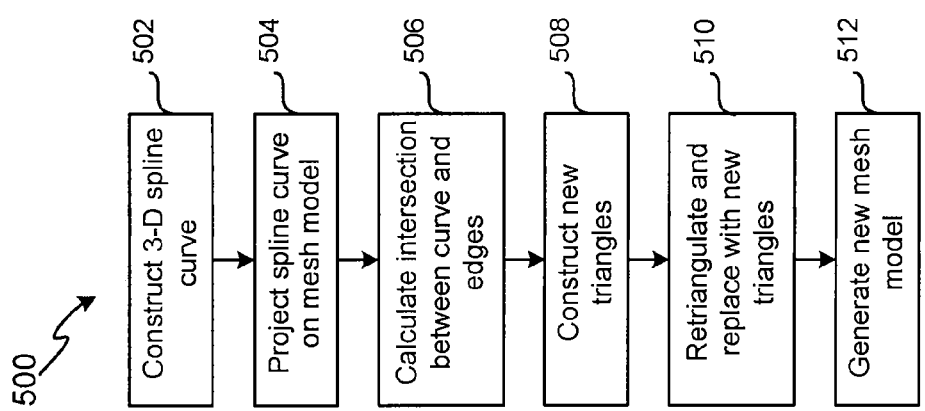

For the generic tooth, the crown and root geometry can be extracted from the generic tooth model. After such extraction or segmentation, the crown/root mesh can be suitably generated. For example, with reference to FIGS. 5A and 5B, a process 500 for automated crown/root mesh generation can comprise the construction of the 3D spline curve (502), wherein control points on the transition area between the tooth crown and root are utilized, such as that illustrated in FIG. 5B. Next, the projection of the 3D spline curve on the tooth mesh model (504) can be conducted. A calculation of the intersection between the projected curve and the edges of triangle faces of the mesh (506) can then be made to facilitate the construction of new triangles (508). In this process, the three original vertices of the intersected triangle and the two intersection points can be utilized to construct three new triangles, such as by use of the Delaunay triangulation's max-min angle criterion. After such construction, the re-triangulation of the old intersected triangle and replacing that old triangle with the three newly generated triangles (510) can be conducted. Upon re-triangulation and replacement, the generation of new crown/root mesh model (512) can be realized by removing all the faces below/above the projected curve, resulting in a segmented generic tooth crown/root. Processes 502, 504, 506, 508, 510 and 510 can be provided through any known conventional techniques for providing such functions, or hereinafter devised.

Once the crown of the generic tooth template has been segmented, automated creation of landmarks on the generic crown (212) can be performed prior to morphing with the patient tooth crown model. In accordance with an exemplary embodiment, with reference to FIGS. 4A-4D, landmarks can be created on a crown sphere (402) and then the landmarks can be projected onto a crown surface (404). For example, a tooth crown can be suitably mapped to a sphere by central projection, as illustrated in FIG. 4B. The landmarks can be created on the sphere through appropriate distribution on each of a plurality of cross-sections, e.g., cross-sections through the Z-axis, perpendicular to the X-Y plane. For example, as illustrated in a representative cross-section shown in FIG. 4C, a plurality of landmarks 406 can be created on a sphere 410 with appropriate distribution. The number of landmarks 406 can be determined through parameters such as the number of planes to be considered while sweeping through the Z-axis, and the number of points selected for each plane. Once landmarks 406 are created on the crown sphere (402), landmarks can be suitably projected onto the crown surface, such as landmarks 408 projected onto the crown surface in FIG. 4C, and landmarks 408 illustrated in FIG. 4D that comprise landmarks 408 projected onto a scan of a patient's crown 420 and a generic tooth crown 430 comprising a root and crown template. Such an automated generation can be facilitated by one or more algorithms within a tooth modeling system, and can be suitably computed for each patient tooth and generic tooth. The plurality of landmarks 408 on generic tooth crown 430 and the corresponding landmarks 408 on the patient tooth crown 420 will be used for calculating the morphing function.

With reference again to FIG. 2, method 204 for generating a patient tooth crown model can comprise the generation of an initial patient tooth model without root (214), i.e., generation of a crown tooth model, automated detection of the crown geometry (216) and the automated creation of landmarks on the patient crown tooth model (218). Generating the crown tooth model (214) can be suitably realized by various known methods and techniques, including various conventional scanning techniques used in computational orthodontics for creating IDDS and the like.

For example, such an IDDS can be derived from the above methods and/or as set forth in U.S. Pat. No. 6,217,325, also assigned to Align Technology, Inc. In an exemplary embodiment, to obtain an IDDS, the patient's teeth may be scanned or imaged using well known technology, such as X-rays, three-dimensional X-rays, computer-aided tomographic images or data sets, magnetic resonance images, etc. Methods for digitizing such conventional images to produce data sets useful in the present invention are well known and described in the patent and medical literature. Usually, however, an IDDS procurement will rely on first obtaining a plaster cast of the patient's teeth by well known techniques, such as those described in Graber, Orthodontics: Principle and Practice, Second Edition, Saunders, Philadelphia, 1969, pp. 401-415. After the tooth casting is obtained, it can be digitally scanned using a conventional laser scanner or other range acquisition system to produce the IDDS. The data set produced by the range acquisition system may, of course, be converted to other formats to be compatible with the software which is used for manipulating images within the data set, as described in more detail in U.S. Pat. No. 6,217,325. General techniques for producing plaster casts of teeth and generating digital models using laser scanning techniques are described, for example, in U.S. Pat. No. 5,605,459.

In addition, there are a variety of range acquisition systems, generally categorized by whether the process of acquisition requires contact with the three dimensional object. A contact-type range acquisition system utilizes a probe, having multiple degrees of translational and/or rotational freedom. By recording the physical displacement of the probe as it is drawn across the sample surface, a computer-readable representation of the sample object is made. A non-contact-type range acquisition device can be either a reflective-type or transmissive-type system. There are a variety of reflective systems in use. Some of these reflective systems utilize non-optical incident energy sources such as microwave radar or sonar. Others utilize optical energy. Those non-contact-type systems working by reflected optical energy further contain special instrumentation configured to permit certain measuring techniques to be performed (e.g., imaging radar, triangulation and interferometry). For example, a preferred range acquisition system is an optical, reflective, non-contact-type scanner. Non-contact-type scanners are preferred because they are inherently nondestructive (i.e., do not damage the sample object), are generally characterized by a higher capture resolution and scan a sample in a relatively short period of time. One such scanner is the Cyberware Model 15 manufactured by Cyberware, Inc., Monterey, Calif. Moreover, either non-contact-type or contact-type scanners may also include a color camera, that when synchronized with the scanning capabilities, provides a means for capturing, in digital format, a color representation of the sample object.

Upon generating the crown tooth model, automatic detection of the crown geometry (216) is conducted to prepare the tooth model for creation of landmarks. For the patient tooth model, the crown geometry can be segmented from the entire tooth using any conventional process for segmentation of crowns from teeth. Upon detecting the crown geometry, the automated creation of landmarks on the patient crown tooth model can be provided, such as the techniques (212) utilized on the generic crown model, e.g., those illustrated by FIGS. 4A-4D.

Upon generation of the generic tooth model (202) and the crown tooth model (204), generation of the complete tooth model (206) can be conducted through combination/morphing of the generic tooth model with the corresponding patient tooth crown model. In accordance with an exemplary embodiment, a method for generating a complete tooth model (206) can comprise calculating the morphing function (220), calculating the patient root (222), stitching the patient crown to the patient root (224), smoothing the root-crown transition area (226) and conducting interactive adjustment of the patient root if necessary (228). Such processes can be completely conducted for individual teeth before proceeding to any other teeth, conducted concurrently, or any other combination thereof.

For calculating of the morphing function 220, in accordance with an exemplary embodiment, a thin-plate spline can be utilized to calculate the morphing function by the created landmarks. Use of such a thin-plate spline can minimize the deformation energy effects, e.g., minimize the degree or extent of bent in the resulting surface between created landmarks. In addition, the Euclidian points distance or surface shortest distance between landmarks is utilized for calculation of the morphing function through:

$$\iint_{R^2} \left(\frac{\partial^2 f}{\partial^2 x^2}\right)^2 + 2\left(\frac{\partial^2 f}{\partial x \partial y}\right)^2 + \left(\frac{\partial^2 f}{\partial^2 y^2}\right)^2 dxdy$$

Once the morphing function is calculated (220), the patient root geometry can be suitably calculated (222), such as by applying the morphing function on the generic root model.

Figure 8A:
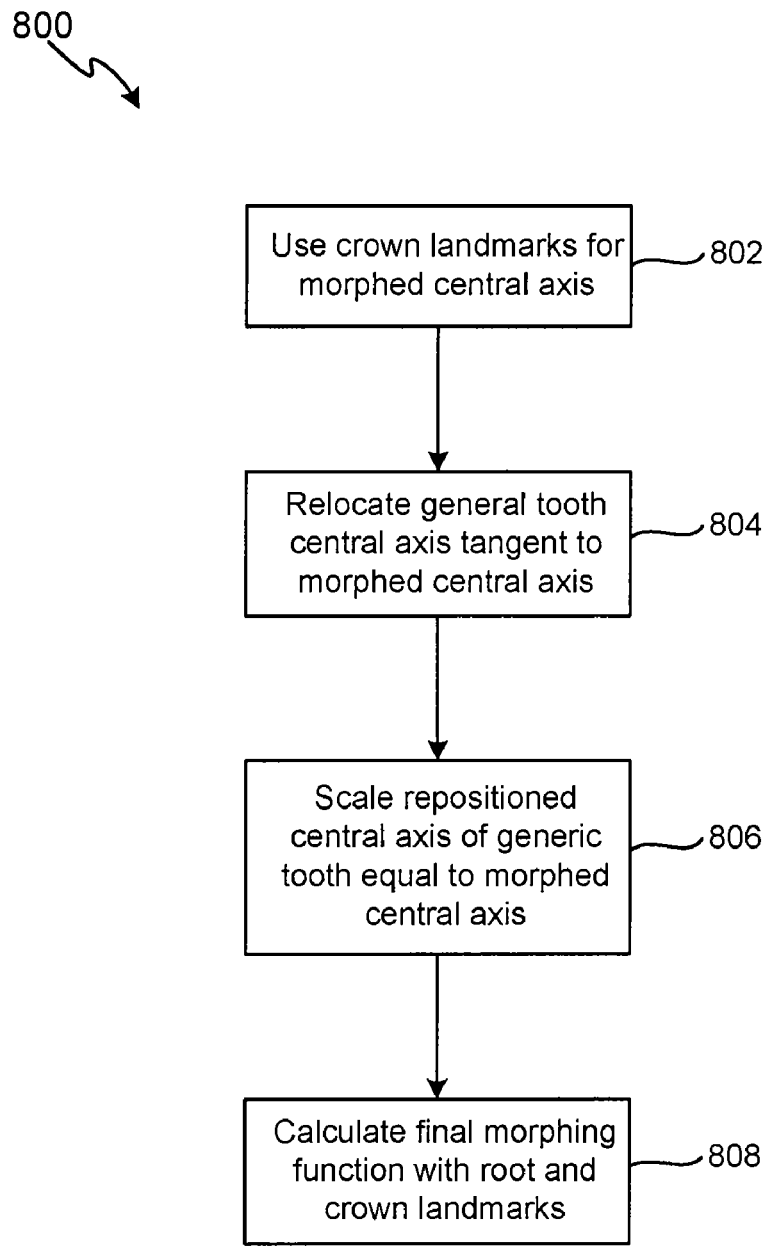
FIGS. 8A-8C illustrate a flow diagram and a graphical representations and curves for an exemplary method for morphing control by root landmarks in accordance with an exemplary embodiment of the present invention.
Figures 8B, 8C:
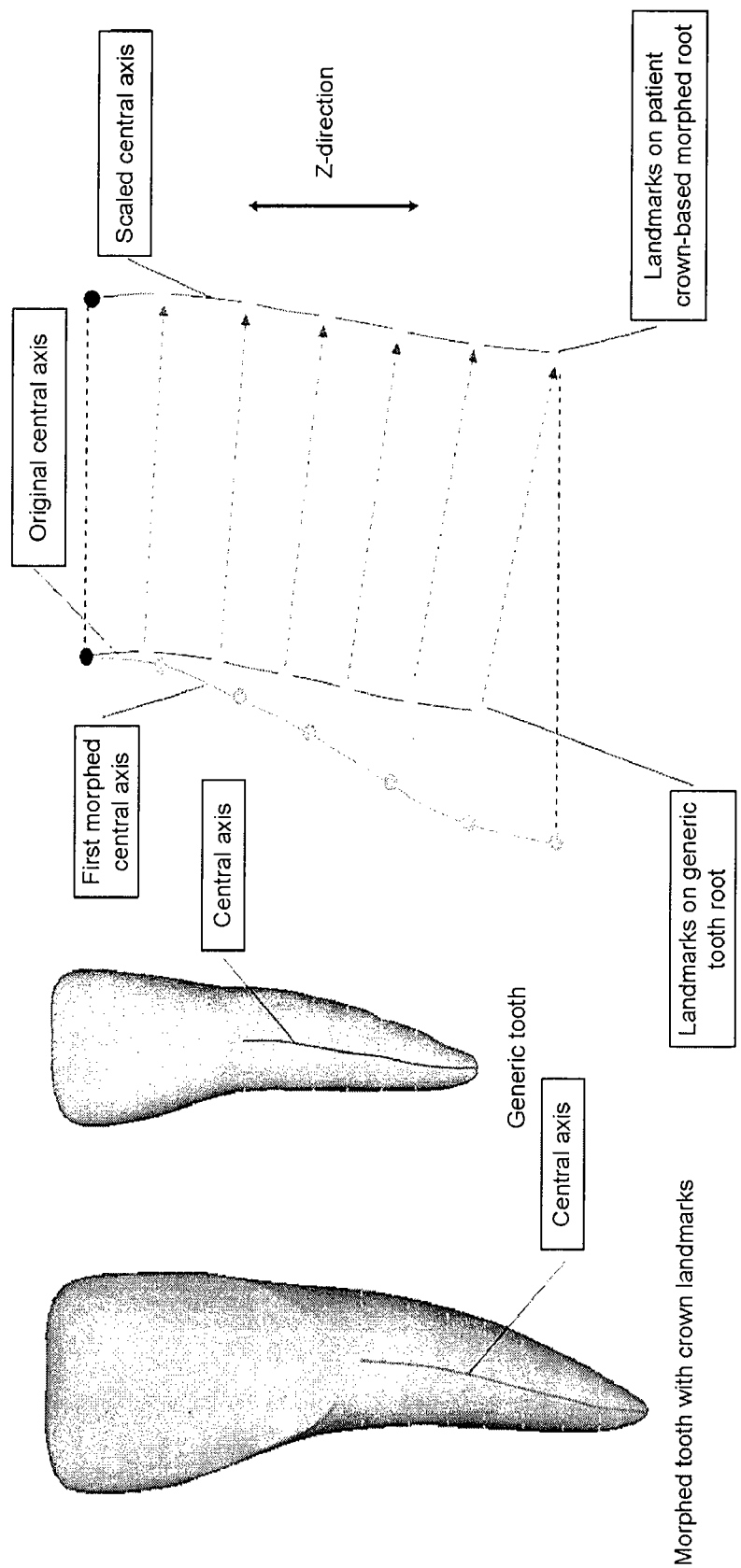

In some cases, the patient crown is quite different from the generic tooth crown. When this occurs, using only the crown landmarks for morphing control may prove insufficient, as the root shape and direction may be difficult to control. In accordance with another exemplary embodiment, improved morphing control can be realized by creating landmarks on the root central axis. For example, with reference to FIG. 8A, in the first morphing process, the crown landmarks can be utilized to calculate the initial morphing function, which is used to obtain a morphed central axis (802), such as illustrated in FIG. 8B. Next, the central axis of the generic tooth can be suitably moved to be tangent to the morphed central axis (804), such as illustrated in FIG. 8C. After movement of the central axis of the generic tooth, the repositioned central axis of the generic tooth can be suitably scaled such that its length is equal to the morphed central axis in the Z-direction. As a result, both the crown landmarks and the root landmarks and can be then utilized to calculate the final morphing function.

Figure 6A:
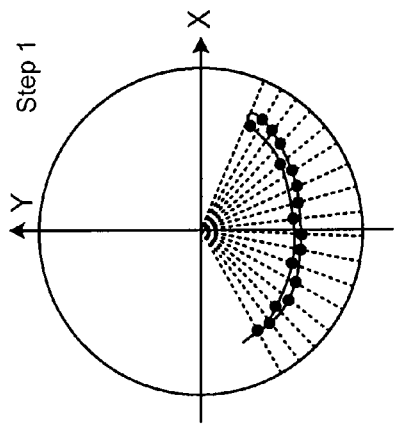
Figure 6A:
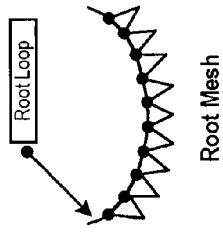
Figure 6A:
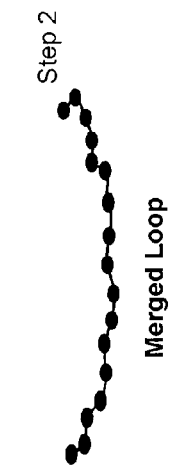
Figure 6A:
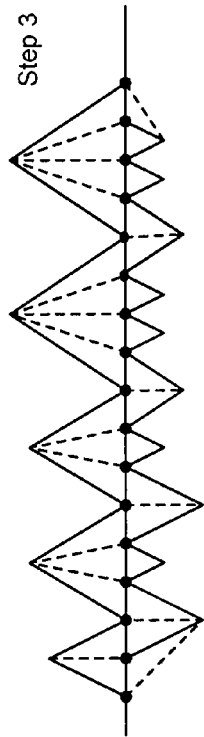
Figure 6A:
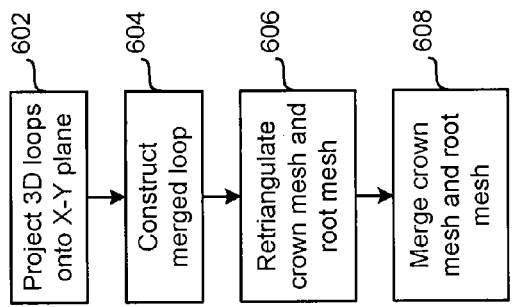

After calculation of the patient root (222) through morphing of the generic tooth root, the patient crown is stitched to the patient root to generate the complete 3D tooth model (224). To facilitate stitching, the crown mesh and the root mesh are suitably merged. For example, with reference to FIG. 6A, the stitching process comprises the projecting of the 3D loops onto the X-Y plane (602), such as illustrated in FIG. 6B. Since the projected loops are homogeneous to a circle, the loop vertices can be re-sorted by angle to construct a merged loop (604), such as illustrated in FIG. 6C. Next, re-triangulation of the crown mesh and the root mesh can be conducted (606). Upon re-triangulation, the crown mesh and root mesh can be merged (608) to obtain a topologically correct complete tooth mesh.

Figure 7B:
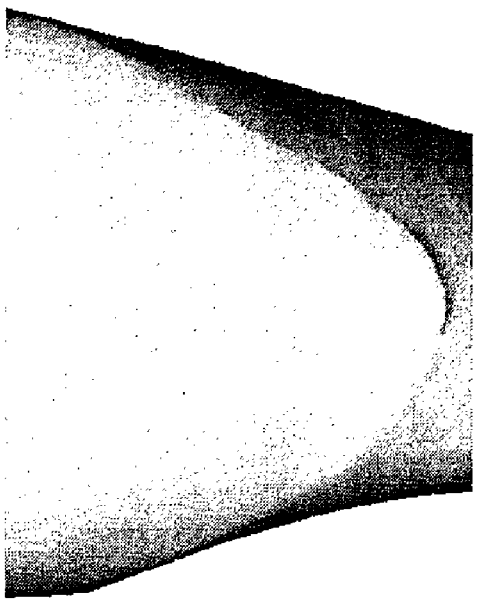
FIGS. 7A and 7B illustrate exemplary three-dimensional tooth models for stitching of the crown and root with and without smoothing processes, respectively, in accordance with exemplary embodiments of the present invention.
Figure 7A:
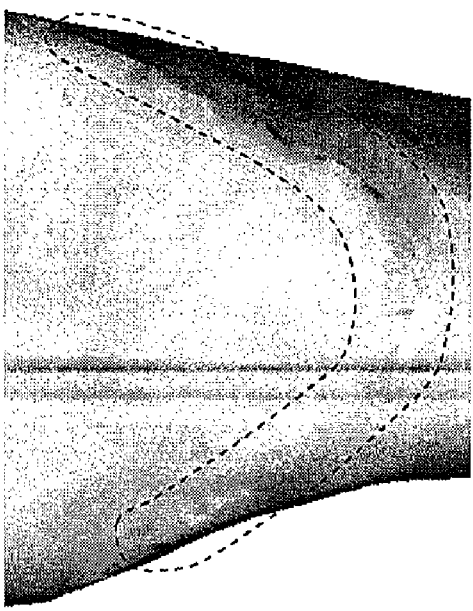

After stitching (224), the crown-root transition area of the complete tooth model can be suitably smoothed (226) to improve the model. For example, with reference to FIG. 7A, after the stitching process, the transition area may not be very smooth. However, through use of a suitably smoothing algorithm, the stitching can be suitably smoothed, such as illustrated in FIG. 7B. The smoothing algorithm operates as a filter to essentially remove "noise" from the stitched points within the transition area. For example, the algorithm can identify or target a first point, then observe neighboring points to suitably tweak or otherwise adjust the first point to smooth out the stitching. The algorithm can be suitably conducted for each tooth within the patient. Such an algorithm can also comprise various formats and structures for providing the smoothing function.

Figures 9A, 9B:
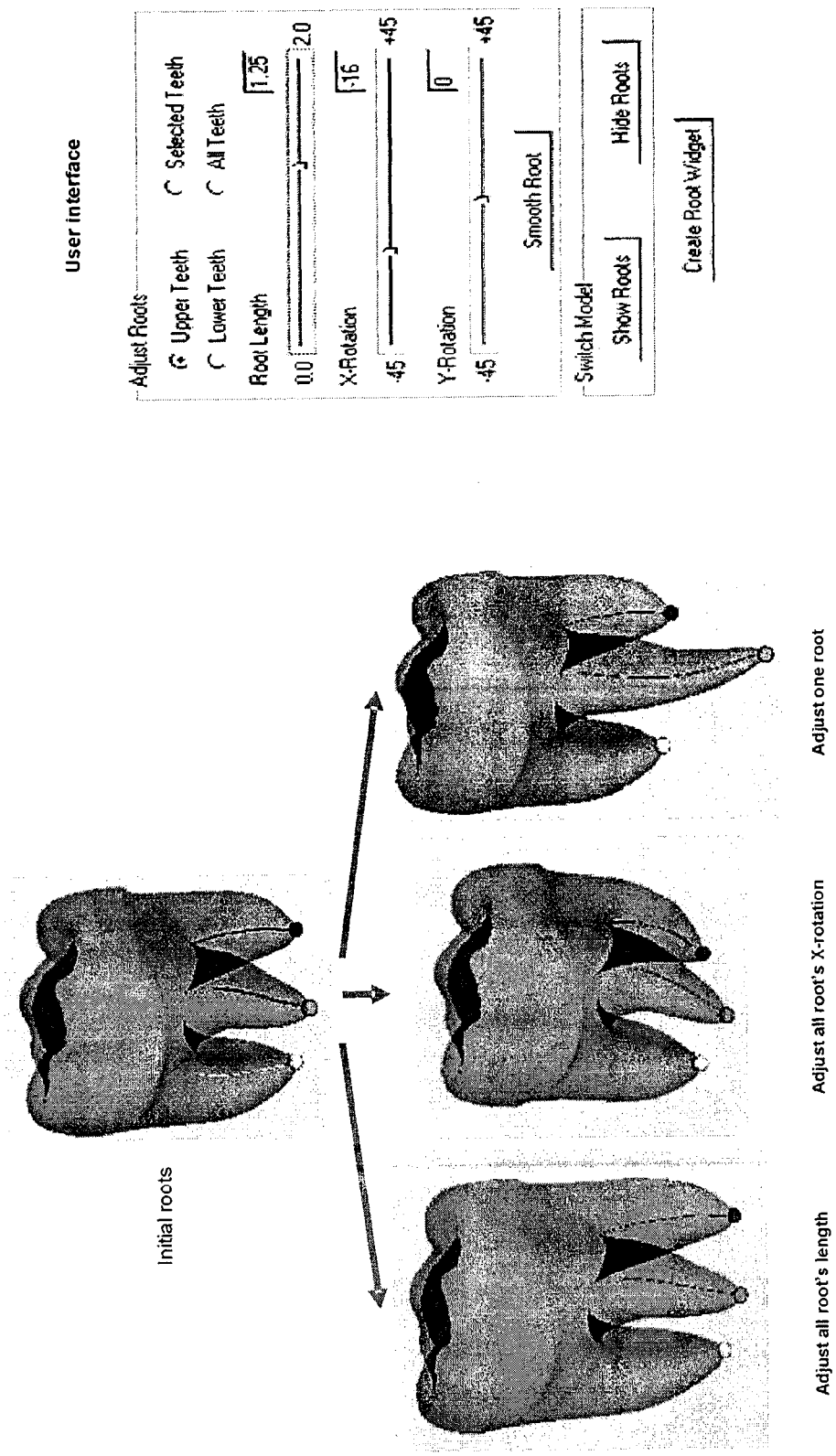
FIGS. 9A and 9B illustrate exemplary three-dimensional complete tooth models and an exemplary user interface for interactive root adjustment in accordance with an exemplary embodiment of the present invention.

After smoothing of the crown-root transition (226), interactive root adjustment (228) can be provided. With reference to FIG. 9A, the complete 3D root model can be adjusted by length or rotation on demand. For example, all the length of all roots, adjust all roots X-rotation, or the adjustment of one root. Such adjustment can be suitably carried out through a user interface, such as that illustrated in FIG. 9B, and/or automatically by the modeling system, to achieve a desired criteria. As a result, the complete tooth model is generated for use in facilitating treatment.

As briefly discussed, in some instances, after generation of the complete tooth model, the generated root shape may vary from the actual root shape due to the individual features of the patient. With reference again to FIG. 1 in accordance with an exemplary embodiment, further adjustment of the complete tooth model for the tooth can be provided through detailed adjustment modeling 108. For example, additional patient root information regarding features or characteristics of the actual root, such as can be obtained from X-ray imaging information provided from a radiograph 107, can be suitably utilized by tooth modeling system 112 to address the variations in root shape between a generic root and an actual root shape for a patient so as to yield a root shape on complete tooth model 105 which more closely approximates the actual root shape of the actual teeth.

Such additional actual root information can comprise various formats and generated in various manners. For example, X-ray imaging information can comprise, for example, panoramic, periapical, bitewing, cephalometric or other like information, for facilitating further detailed modeling. In addition, since such X-ray imaging information generally comprises a 2D image, the X-ray information can be considered approximately as a 2D projection from the facial side to the lingual side. As a result, the further detailed adjustment is based on one-view information, wherein the algorithm suitably makes the modeled root shape coincide with the actual root shape based on such one-view information.

Figure 11A:
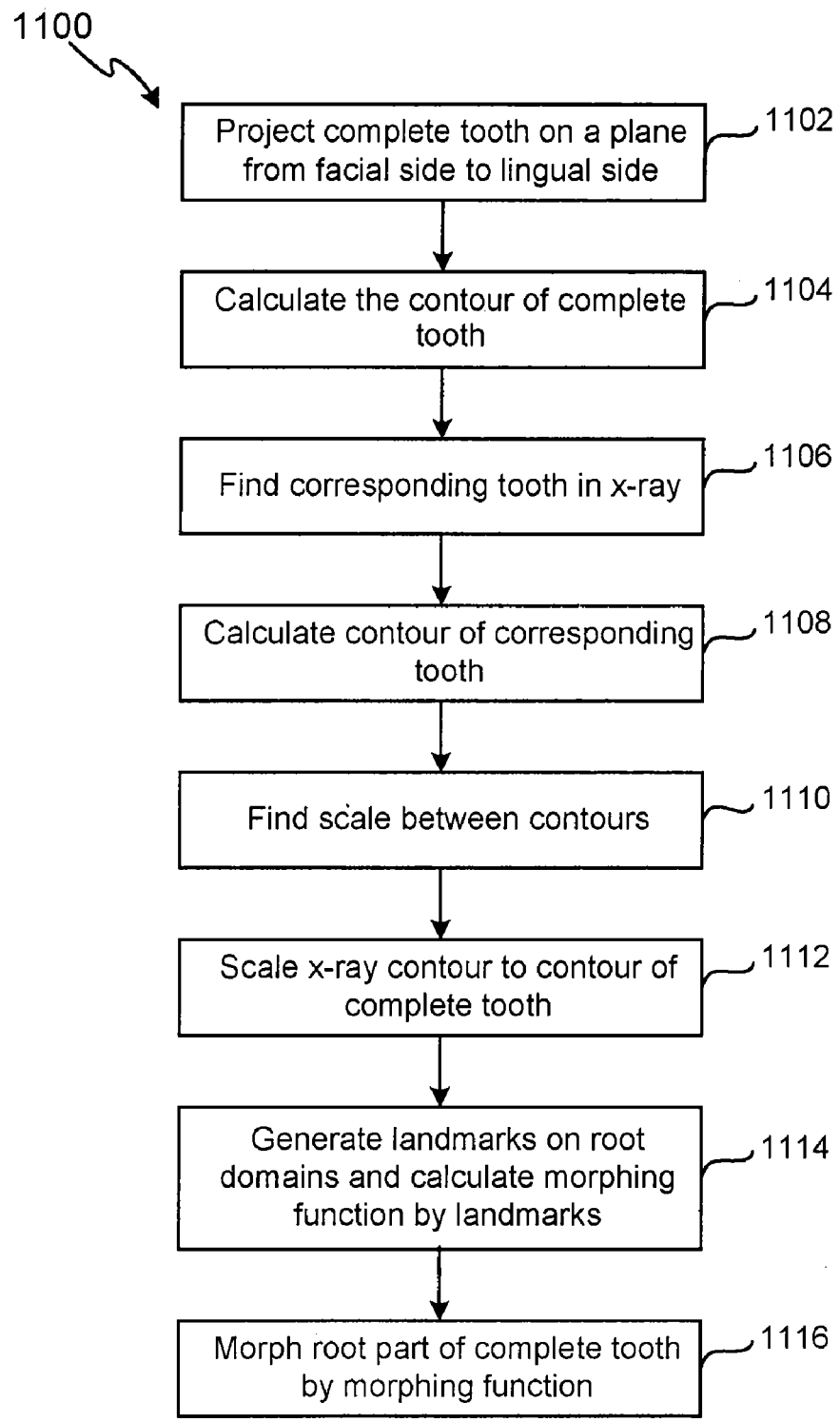

For example, with reference to FIG. 11A, a method for detailed adjustment modeling can begin with the projection of the complete tooth model, e.g., one derived after morphing/combination (206) of method 200, on a single plane, whose normal is from a tooth's facial side to a tooth's lingual side (1102). Next, the contour of the complete tooth can be calculated (1104) and defined, such as the tooth contour A illustrated in FIG. 11B. The corresponding patient tooth can be suitably identified from the X-ray information, such as from panoramic X-ray image (1106), and the contour of the corresponding tooth can also be calculated from that X-ray image (1108) and defined, such as the tooth contour B illustrated in FIG. 11C. Any conventional methodology or process for calculation and/or determination of contours can be readily utilized for determining the contours of tooth A and tooth B. Next, the scaling in size between the complete tooth contour (e.g., contour A), and the corresponding patient tooth contour (e.g., contour B) can be determined (1110), and then the corresponding patient tooth contour can be scaled to have to have the same crown contour as the complete tooth contour (1112). In accordance with another exemplary embodiment, instead of scaling complete tooth contour (1112), thin-plate spline based morphing function can be used to deform the corresponding patient tooth crown contour to the complete tooth crown contour. For example, the morphing function can be calculated by the landmarks on the corresponding patient tooth crown contour and complete tooth crown contour. Landmarks can then be generated (1114) on the root domain of the complete tooth contour (e.g., contour A), and the corresponding tooth contour (e.g., contour B), such as illustrated with reference to FIGS. 11D and 11E. Based on the generated landmarks, and the calculation of the morphing function, the complete tooth contour can be suitably morphed onto a projection plane (1116), such as illustrated in FIG. 11F. Such morphing can be conducted through similar processes as disclosed in morphing/combining process 206, e.g., by calculating a morphing function (220) and applying the morphing function of the root portion (222). Accordingly, a complete tooth model for any one and/or all teeth of a patient, suitably adjusted through an accounting of a patient's individual and/or specialized features and characteristics, can be realized.

Figure 10A:
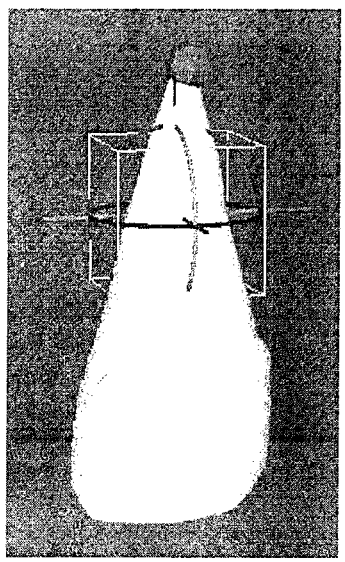
FIGS. 10A-10C illustrate exemplary diagrams for root widgets in accordance with an exemplary embodiment of the present invention.
Figure 10B:
Figure 10C:
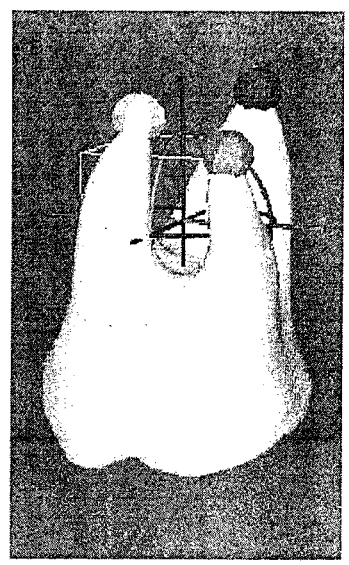

The complete tooth models comprising root portions can be used to further facilitate planning and treatment processes. Additional steps can also be introduced to further improve the planning and treatment processes. As an example, to create an enhanced clinical meaningful movement, a root widget can be created for use in manipulating the tooth. In particular, with reference to FIGS. 10A-10C, a clinically meaningful root widget can be created at the center of resistance of a tooth. In this embodiment, the center of rotation of the tooth is considered to be at approximately ⅓ of the tooth length from the root apex along the vertical axis of the tooth. The axis of the tooth can be established by any conventional methodology or process for establishing axis and/or coordinate systems within teeth.

Another treatment process that can be implemented is to monitor the speed of root movement for a tooth to determine which teeth are moving more aggressively. Use of the root geometry can be readily used to facilitate this calculation. For example, the movement speed from a stage n to a stage n+1 is defined by the formula:

$$m = \int_s dist(x, y, z) \, ds$$

where (x,y,z) is the point on the root surface and dist(x,y,z) is the moving distance of this point from stage n to a stage n+1. The dist(x,y,z) can be computed by the length of the trajectory of the point (x,y,z) from its position a stage n to the position at stage n+1. As a result, treatment adjustments to teeth based on their speed of root movement can be conducted to further enhance the treatment process.

The present invention has been described above with reference to various exemplary embodiments. However, those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, e.g., various of the component and methodologies and/or steps may be deleted, modified, or combined with other components, methodologies and/or steps. Moreover, it is understood that various of the methods and steps disclosed herein, such as generating of IDDS, construction of 3D spline curves, identifying or gingival curves or other processes can also comprise any other conventional techniques, or any later developed techniques, for facilitating such methods and steps. These and other functions, methods, changes or modifications are intended to be included within the scope of the present invention, as set forth in the following claims.

The invention claimed is:

1. A computer-implemented method for modeling of a complete tooth of a patient to facilitate dental and/or orthodontic treatment, said computer-implemented method for modeling comprising:

generating at least one patient digital tooth model comprising a crown component;

generating at least one generic digital tooth model corresponding to said at least one patient digital tooth model, said at least one generic digital tooth model comprising both root and crown components; and morphing said at least one patient digital tooth model with said at least one generic digital tooth model to provide a complete digital tooth model of the patient wherein morphing comprises:

generating an initial morphing function;

calculating a patient root component from said initial morphing function;

conducting interactive adjustment of said patient root component comprising adjusting by at least one of length and rotation;

stitching a corresponding patient crown component to said patient root component, wherein stitching comprises:

projecting three-dimensional loops onto an x-y plane;

constructing a merged loop;

re-triangulating a crown mesh and a root mesh; and merging said crown mesh with said root mesh;

utilizing crown landmarks to calculate the initial morphing function, which is used to determine a morphed central axis;

repositioning a central axis of said generic tooth model to be tangent to said morphed central axis;

scaling said repositioned central axis of said generic tooth model to be substantially equal to said morphed central axis in a z-direction; and calculating a final morphing function through use of both the crown landmarks and the root landmarks from said generic tooth model and said patient tooth model.

2. The computer-implemented method according to claim 1, wherein generating said at least one generic digital tooth model comprises:

providing a generic tooth model template comprising a generic root and a generic crown;

segmenting of said generic crown from said generic root within said generic tooth model template; and automatically creating landmarks on said generic crown.

3. The computer-implemented method according to claim 2, wherein providing the generic tooth model template comprises:

acquiring data representing a physical tooth model;

setting up a generic tooth coordinate system;

constructing of a generic tooth digital model; and creating of template file(s) associated with said generic tooth.

4. The computer-implemented method according to claim 3, wherein generating a generic tooth model template further comprises identifying of a gingival curve associated with said generic tooth model prior to creating of template file(s) associated with said generic tooth.

5. The computer-implemented method according to claim 3, wherein acquiring data representing a physical tooth model comprises scanning of the physical tooth model to generate three-dimensional data.

6. The computer-implemented method according to claim 5, wherein scanning of the physical tooth model comprises scanning a generic root shape for a specific tooth type and a generic crown shape for said specific tooth type to generate said three-dimensional data.

7. The computer-implemented method according to claim 3, further comprising decimating of said acquired data.

8. The computer-implemented method according to claim 2, wherein segmenting of said generic crown from said generic root within said generic tooth model template comprises parceling out a generic crown component to facilitate mapping of said generic crown component during the creating of landmarks.

9. The computer-implemented method according to claim 2, wherein creating landmarks on said generic crown comprises creating landmarks on a crown sphere for said generic tooth model.

10. The computer-implemented method according to claim 9, wherein creating landmarks on a crown sphere for said generic tooth model comprises mapping said landmarks on the crown sphere appropriately distributed on cross-sections.

11. The computer-implemented method according to claim 2, wherein creating landmarks on said generic crown further comprises projecting said landmarks onto a crown surface.

12. The computer-implemented method according to claim 2, wherein segmenting of said generic crown from said generic mesh further comprises generating crown and root mesh.

13. The computer-implemented method according to claim 12, wherein generating crown and root mesh comprises:
constructing a three-dimensional spline curve through control point on a transition area between patient tooth crown and root;
projecting said three-dimensional spline curve on a tooth mesh having triangle faces;
calculating an intersection between a projected curve and edges of said triangle faces; and
construct three new triangles using three original vertices of an intersected triangle and two intersection points.

14. The computer-implemented method according to claim 13, wherein generating crown and root mesh further comprises:
re-triangulating said intersected triangle and replace with said three new triangles; and
removing all faces below said projected curve to generate a new tooth mesh model comprising tooth crown.

15. The computer-implemented method according to claim 1, wherein generating at least one patient tooth model comprises:
generating a patient crown tooth model without a root component;
detecting of crown geometry from said patient crown tooth model; and
automatically creating landmarks on said patient crown tooth model.

16. The computer-implemented method according to claim 1, wherein stitching a corresponding patient crown component to said patient root component comprises stitching said patient crown component for a particular tooth with said patient root component corresponding to said particular tooth.

17. The computer-implemented method according to claim 16, wherein stitching said patient crown component for a particular tooth with said patient root component corresponding to said particular tooth is conducted for each tooth of a patient.

18. The computer-implemented method according to claim 1 wherein morphing further comprises smoothing the root-crown transition area.

19. The computer-implemented method according to claim 1, wherein calculating a morphing function comprises using a thin-plate spline.

20. The computer-implemented method according to claim 1, wherein calculating a patient root component comprises applying said initial morphing function on said generic tooth model.

21. The computer-implemented method according to claim 1, wherein constructing said merged loop comprises resorting vertices of said merged loop.

22. The computer-implemented method according to claim 1, wherein said computer-implemented method further comprises detailed adjustment modeling of said complete tooth model.

23. The computer-implemented method according to claim 22, wherein said detailed adjustment modeling comprises using actual root information associated with a particular tooth of the patient.

24. The computer-implemented method according to claim 23, wherein said detailed adjustment modeling comprises using actual X-ray imaging information associated with the particular tooth of the patient.

25. The computer-implemented method according to claim 24, wherein said detailed adjustment modeling comprises:
projecting of said complete tooth model on a single plane from a facial side to a lingual side;
calculating a contour of said complete tooth model;
locating a corresponding patient tooth from said X-ray information;
calculating a contour of said corresponding patient tooth;
determining a scale between said contour of said complete tooth model and said contour of said corresponding patient tooth; and
scaling said contour of said corresponding patient tooth to said contour of said complete tooth model.

26. The computer-implemented method according to claim 25, wherein said detailed adjustment modeling comprises:
generating landmarks on root domains of said complete tooth model's said contour and said corresponding patient tooth's said contour; and
morphing said root domains on said single plane.

27. The computer-implemented method according to claim 1, wherein said computer-implemented method further comprises creating a root widget for manipulating tooth movement.

28. The computer-implemented method according to claim 1, wherein said computer-implemented method further comprises monitoring speed of movement of a tooth using root geometry.

29. A computerized system for modeling of tooth root and crown of a patient to facilitate dental and/or orthodontic treatment, said computerized modeling system comprising:

a microprocessor comprising a plurality of algorithms;
a memory device; and
wherein said computerized modeling system is configured for generating:
a three-dimensional digital crown model for a particular tooth of the patient; and
a three-dimensional digital generic model comprising both a generic crown component and a generic root component, said three-dimensional generic model configured for said particular tooth of said three-dimensional crown model; and
wherein said computerized modeling system is configured for morphing said a three-dimensional crown model with said three-dimensional generic model to yield a complete three-dimensional root and crown tooth model for said particular tooth, wherein morphing comprises:
generating an initial morphing function;
calculating a patient root component from said initial morphing function;
conducting interactive adjustment of said patient root component comprising adjusting by at least one of length and rotation;
stitching a corresponding patient crown component to said patient root component, wherein stitching comprises:
projecting three-dimensional loops onto an x-y plane;
constructing a merged loop;
re-triangulating a crown mesh and a root mesh; and
merging said crown mesh with said root mesh;
utilizing crown landmarks to calculate the initial morphing function, which is used to determine a morphed central axis;
repositioning a central axis of said generic tooth model to be tangent to said morphed central axis;
scaling said repositioned central axis of said generic tooth model to be substantially equal to said morphed central axis in a z-direction; and
calculating a final morphing function through use of both the crown landmarks and the root landmarks from said generic tooth model and said patient tooth model.

30. The computerized modeling system according to claim 29, wherein said three-dimensional generic model comprises a generic tooth template generated from scanning of a physical model for said particular tooth.

31. The computerized modeling system according to claim 30, wherein said computerized modeling system is configured for segmenting said generic crown component from said generic root component, and for automated creation of landmarks on said generic crown component.

32. The computerized modeling system according to claim 31, wherein said computerized modeling system is configured for automated creation of landmarks on a crown component of said particular tooth.

33. The computerized modeling system according to claim 29, wherein said computerized modeling system is configured for smoothing a crown-root transition area of said complete three-dimensional root and crown tooth model.

34. The computerized modeling system according to claim 29, wherein said computerized modeling system is configured for interactive root adjustment.

35. A non transitory computer readable medium storing instructions that when executed by a computing device cause the computing device to perform a method including:
generating a plurality of actual patient tooth models corresponding to each of a plurality of teeth of a patient, each of said plurality of patient tooth models comprising corresponding crown components;
generating a plurality of generic tooth models corresponding to said plurality of patient tooth models, said plurality of generic tooth models comprising both generic root and generic crown components; and
morphing each of said plurality of patient tooth models with a corresponding one of said plurality of generic tooth models to provide a complete tooth modeling for said plurality of teeth of the patient, wherein morphing comprises:
generating an initial morphing function;
calculating a patient root component from said initial morphing function;
conducting interactive adjustment of said patient root component comprising adjusting by at least one of length and rotation;
stitching a corresponding patient crown component to said patient root component, wherein stitching comprises:
projecting three-dimensional loops onto an x-y plane;
constructing a merged loop;
re-triangulating a crown mesh and a root mesh; and
merging said crown mesh with said root mesh;
utilizing crown landmarks to calculate the initial morphing function, which is used to determine a morphed central axis;
repositioning a central axis of said generic tooth model to be tangent to said morphed central axis;
scaling said repositioned central axis of said generic tooth model to be substantially equal to said morphed central axis in a z-direction; and
calculating a final use of both the crown landmarks and the root landmarks from said generic tooth model and said patient tooth model.

36. The digital representations according to claim 35, wherein generating a plurality of generic tooth models comprises generating a specific root component for a specific type of tooth.

37. The digital representations according to claim 36, wherein said process further comprises detailed adjustment modeling using actual root information associated with a particular tooth of the patient.

* * * * *